United States Patent [19]

Hidalgo et al.

[11] Patent Number: 4,463,017
[45] Date of Patent: Jul. 31, 1984

[54] COMPOSITION FOR TOPICAL ADMINISTRATION

[75] Inventors: Jaime Hidalgo, La Tour-de-Peilz; Rolf Jost, Clarens, both of Switzerland

[73] Assignee: Societe d'Assistance Technique pour Produits Nestle S.A., Lausanne, Switzerland

[21] Appl. No.: 302,183

[22] Filed: Sep. 14, 1981

Related U.S. Application Data

[63] Continuation of Ser. No. 112,151, Jan. 14, 1980, abandoned.

[30] Foreign Application Priority Data

Jan. 16, 1979 [FR] France ................. 79 00952

[51] Int. Cl.$^3$ .......... A61K 7/15; A61K 7/42; A61K 47/00
[52] U.S. Cl. ................. 424/359; 252/107; 424/59; 424/73; 424/168; 424/177; 424/358; 424/361; 424/365; 426/42
[58] Field of Search ............ 424/177, 359, 168; 426/42

[56] References Cited

U.S. PATENT DOCUMENTS

| | | | |
|---|---|---|---|
| 597,378 | 1/1898 | Backhaus | 426/42 |
| 2,023,359 | 12/1935 | Sirek | 424/359 |
| 2,585,225 | 2/1952 | Carlson | 426/42 |
| 4,076,800 | 2/1978 | Marsh et al. | 424/359 |
| 4,179,333 | 12/1979 | Braeumer et al. | 424/359 |
| 4,209,503 | 6/1980 | Shah | 424/359 |

FOREIGN PATENT DOCUMENTS

| | | | |
|---|---|---|---|
| 519236 | 12/1955 | Canada | 426/42 |
| 576467 | 5/1959 | Canada | 426/42 |
| 1949207 | 9/1969 | Fed. Rep. of Germany | 424/365 |
| 2019235 | 11/1971 | Fed. Rep. of Germany | 424/365 |
| 820846 | 7/1937 | France | 424/359 |
| 1280561 | 11/1961 | France | 426/42 |
| 1580913 | 9/1969 | France | 424/365 |
| 37-13718 | 9/1962 | Japan | 426/42 |
| 51-5465 | 2/1976 | Japan | 426/42 |
| 16016 | of 1897 | United Kingdom | 426/42 |
| 119430 | 10/1918 | United Kingdom | 426/42 |
| 752922 | 7/1956 | United Kingdom | 426/42 |

OTHER PUBLICATIONS

Burnett, Amer. Perf. & Cosm., 10/63 vol. 78, pp. 69-72.
Derwent Abstract No. 457353/25, 5/6/78, Zimzik.

*Primary Examiner*—Dale R. Ore
*Attorney, Agent, or Firm*—Vogt & O'Donnell

[57] ABSTRACT

The invention relates to a composition for topical administration. This composition contains an active proportion, namely from 0.5 to 25% by weight and preferably from 2 to 10% by weight, of a hydrolysate of lactalbumin obtained solely by the action of an endopeptidase, said hydrolysate consisting essentially of peptides having a molecular weight of from 200 to 5000.

This composition may be used as a cosmetic or therapeutic agent.

3 Claims, No Drawings

COMPOSITION FOR TOPICAL ADMINISTRATION

This is a continuation of application Ser. No. 112,151 filed Jan. 14, 1980, now abandoned.

This invention relates to a composition for topical application which may be used as a cosmetic or therapeutic agent.

It is known that, generally speaking, preparations based on amino acids have a beneficial effect on the skin tissues and that they enter into the composition of numerous pastes, ointments, balms, salves, masks, creams, milks and other skin-care products which enhance hygiene and beauty. These preparations are frequently products of the hydrolysis, particularly the enzymatic hydrolysis, of animal protein extracts or proteins such as casein or lactalbumin (whey protein).

Experience has shown that, when used in creams, products of this type, particularly those resulting from the hydrolysis of lactalbumin with a conventional enzymatic system, such as pancreatin, develop unpleasant odours which are very difficult to conceal. Although creams of the type in question may be therapeutically or experimentally used providing they are heavily and suitably perfumed it will readily be appreciated that, even under these conditions, they are totally unsuitable for cosmetic applications.

By contrast, the topical composition according to the present invention is not attended by this inhibiting disadvantage despite the fact that it also contains products emanating from the enzymatic hydrolysis of lactic proteins. It is characterised in that it contains a hydrolysate of lactalbumin obtained solely by the action of an endopeptidase, said hydrolysate consisting essentially of peptides having a molecular weight in the range from 200 to 5000. As used herein, the term "topical" is intended to mean that the composition is adapted for external administration to all areas of the body, including the hair.

This composition contains an effective amount of the hydrolysate, namely from 0.5 to 25% by weight and preferably from 2 to 10%, expressed as dry weight of hydrolysate in the composition as a whole.

As endopeptidase, i.e. as enzyme which breaks specific peptide bonds, in particular inside the polypeptide chains, and in contrast to the exopeptidases which are less specific and begin at the (protein) chain ends, it is possible to use for example enzymatically pure trypsin and/or chymotrypsin. The resulting hydrolysate consists essentially of peptides having a molecular weight in the range from 200 to 5000. Most of the peptides are present in the hydrolysate in free form, the rest being in the form of soluble aggregates. The hydrolysate contains only very minor quantities of higher peptides and of free amino acids. Its composition, which is related to the whey containing the starting lactalbumin, may vary within the following limits, expressed in percent by weight:

| | |
|---|---|
| total nitrogen | 5 to 15 |
| lactose | 0.1 to 18 |
| ash | 2 to 7 |
| fat | 0.1 to 6 |
| water | 1 to 4. |

The pH of the hydrolysate is normally of the order of 6.5 to 8 and preferably in the range from 6.5 to 7.5.

Since the hydrolysate is the active ingredient, the composition intended for cosmetic or topical use normally contains a carrier, an excipient or a vehicle compatible with the method of administration selected. For example, for preparing creams and similar products, a paste-like, semi-fluid or fluid ointment base is used which, of course, is non-toxic to the body and which is capable of being emulsified with the hydrolysate (oil-in-water and water-in-oil emulsion). Examples of ingredients for the base include cetyl alcohol, lanolin, petroleum jelly, liquid paraffin and polyoxyethylene sorbitan esters such as the palmitates, oleates and stearates, and these substances, may all be used either separately or in any combination for preparing the base. This base preferably also contains triglycerides containing essential fatty acids and, optionally, a high proportion of liposoluble vitamins, long-chain fatty alcohols, esters of branched-chain fatty acids and emulsive monoglycerides. Formulations intended for application to base skin desirably have a chemical composition as close as possible to that of human sebum. In certain cases, one or more emulsifiers and/or surfactants may be incorporated in the composition, depending on the type of formulation required.

Finally, the composition generally contains antioxidants, bactericidal and fungicidal agents and, if desired, colourants, pigments and/or perfumes.

The composition according to the invention may also be presented in the form of aqueous dispersions (lotions such as, for example, pre-shave or after-shave lotions), liquid emulsions (body milks, cleansing milks), viscous emulsions (masks), aqueous or anhydrous gels. The composition according to the invention may also be incorporated in make-up foundations and hair care products.

The composition is packaged according to the use and nature of the product. Creams, ointments, etc. are generally filled in jars or tubes whereas lotions, milks or similar products are more frequently packed in bottles or containers capable of dispensing the composition in the form of an aerosol or foam.

The composition according to the invention may be used as a topical cosmetic, for example in the form of a cream or milk, and has a softening, soothing and revitalising effect. It may also be used for preventing inflammation, particularly of the nappy rash type, in babies and for treating the breasts and nipples of nursing mothers. Systematic tests with a 5% cream have produced good results in regard to the suppleness, softness and hydration of the epidermis.

The composition also has a curative use and may be prescribed for the following therapeutic applications: burns, sunburn; dermatitis; weals, chaps, blemishes, cracks and other treatments of scars.

The pharmacological properties of the composition according to the invention include:
- activity on cutaneous necrosis,
- activity in vascular permeability,
- action on the rupture force of cicatrices (increased rupture force).

The invention is illustrated by the following Examples in which the percentages quoted represent percent by weight.

EXAMPLE 1

25 kg of a concentrate of whey proteins obtained by ultrafiltration (approximately 70% of proteins, based on dry matter) are dissolved in 390 kg of de-ionised water at 12° C. The pH of the solution is adjusted to 8.0 with 20% KOH. After heating to 50° C., 150 g of trypsin (NOVO ®; 3 to 6 Anson units per g), are added. This enzyme is free from exopeptidase, lipase and amylase. The whole is then incubated for 1 hour at a constant pH-value, the same KOH solution being used to control the pH. After 1 hour, 100 g of trypsin are added and incubation continued up to a total of 5 hours. The temperature is then raised to 80° C. and maintained for 15 minutes in order to inactivate the enzyme. After cooling to 20° C., the pH is adjusted to 6.8 with 15% HCl. The solution is then concentrated by evaporation to a dry matter content of the order of 30% and freeze-dried. The dry hydrolysate is ground. For storage purposes, the hydrolysate may be stored in tin cans.

The hydrolysate has the following composition:

| | |
|---|---|
| total nitrogen | 10.8% |
| lactose (by difference) | 17.85% |
| ash | 8.05% |
| fats | 3.67% |
| moisture | 1.12% |

It consists essentially of peptides having a molecular weight of 840–980.

Using the hydrolysate, a white protective cream of the oil-in-water emulsion type is prepared by mixing the following ingredients:

| | |
|---|---|
| 1. Polyoxyethylene stearyl ether | 2% |
| Polyoxyethylene cetyl ether | 2% |
| Self-emulsifiable glycerol monostearate | 4% |
| Perhydrosqualene | 5% |
| Soya oil | 5% |
| Mineral oil | 15% |
| Stearic acid | 2% |
| Butyl hydroxy anisole | 0.005% |
| 2. Triethanolamine | 0.4% |
| 3. Carbopol 941 ® | 0.4% |
| Sterile demineralised water | balance to 100% |
| Methyl p-hydroxybenzoate | 0.3% |
| 4. Hydrolysate prepared as described above | 10% |
| Sterile demineralised water | 10% |
| 5. Perfume | as desired |

The procedure comprises heating the fat phase (1) to 80°–85° C. and then heating the sterile demineralised water of phase (3) to the same temperature. The preservative is dissolved in the demineralised water and, after the temperature has fallen to 70° C., the Carbopol ® is added thereto and left to swell for a few hours. The emulsion is prepared at 80° to 85° C. by pouring phase (1) into phase (3) to which phase (2), i.e. the triethanolamine, has previously been added. Emulsification is obtained by stirring for 15 minutes with an impeller. After cooling to 35° C., phase (4) and phase (5) are added. At 25° C., the cream is ready.

This cream has a pleasant protective effect and noticeable healing properties.

For comparison, a white cream is prepared as described above, except that the lactalbumin hydrolysate used is not a hydrolysate containing pure trypsin, but instead a hydrolysate prepared conventionally by treatment with pancreatin. Pancreatin is a relatively complex enzymatic system which, in addition to endopeptidases, contains exopeptidases, lipases and amylases so that the hydrolysate obtained consists essentially of amino acids. The white cream containing this hydrolysate as its active ingredient was found to have the same protective effect and the same healing properties as the cream containing the hydrolysate with pure trypsin, but rapidly developed unpleasant odours which made it unsuitable for cosmetic application.

EXAMPLE 2

10 kg of a concentrate of whey proteins are dissolved in 200 kg of demineralised water, after which the solution is heated with stirring to 50° C. 10 ml of an antifoaming agent (RHODORSIL ®) are added and the pH is adjusted to 8.0 with 1% KOH and then with 5% KOH. 50 g of crystalline porcine trypsin (NOVO 4500 K ®; 25 Anson units per g) are then added, the enzyme being dissolved in approximately 1 liter of whey protein solution. The whole is then incubated with stirring at 50° C. at a pH-value of from 7.9 to 8.0 and, after incubation for 1 hour, another 25 g of trypsin are added. Incubation is then continued for another 2 hours with pH control. Finally, incubation is terminated over a period of another hour without adjusting the pH. The final pH is approximately 7.4. The solution is then heated to 80° C. and kept at that temperature for 15 minutes. After rapid cooling to 20° C., the solution is concentrated by evaporation to a dry matter content of the order of 30%. Finally the concentrate is spray-dried.

The hydrolysate thus obtained has the following composition:

| | |
|---|---|
| total nitrogen: | 11.53% |
| lactose: | 7.5% |
| ash: | 2.8% |
| fats: | 6.0% |
| moisture: | 4.0% |

It consists essentially of peptides of mean molecular weight 1400.

With this hydrolysate, a coloured cream having a protective and fresh effect, of the oil-in-water emulsion type, is prepared from the same complementary ingredients as in Example 1, to which are added:
Ariabel Yellow 300 407 Williams 0.250%
Ariabel Sienna 300 406 Williams 0.2%
Ariabel Black 300 401 Williams 0.04%

This coloured cream is prepared in the same way as the white cream described in Example 1, the colourants being ground in a small part of the final cream which is then dispersed in the rest of the cream.

This coloured cream has a pleasant protective effect and freshens the skin.

For comparison, a coloured cream is prepared in the same way as described above, except that the lactalbumin hydrolysate used is not a hydrolysate containing crystallised trypsin, but instead a hydrolysate prepared conventionally by treatment with pancreatin. The coloured cream containing this hydrolysate as its active ingredient was found to have the same protective effect as the cream containing the hydrolysate with crystallised trypsin, but rapidly developed unpleasant odours which made it unsuitable for cosmetic application.

EXAMPLE 3

A body milk is prepared by mixing the following ingredients:

| | | |
|---|---|---|
| 1. | Stearic acid | 3% |
| | Perhydrosqualene | 7% |
| | Lanolin | 3% |
| | Hexadecyl alcohol | 1.5% |
| 2. | Triethanolamine | 1.7% |
| 3. | Carbopol 940 | 0.2% |
| | Sterile demineralised water | balance to 100% |
| | Methyl p-hydroxybenzoate | 0.3% |
| 4. | Hydrolysate of Example 1 | 5% |
| | Sterile demineralised water | 10% |
| 5. | Perfume | as desired |

The procedure is identical with that described for the white cream of Example 1.

This body milk has a softening effect on the skin.

EXAMPLE 4

A white cream of the water-in-oil emulsion type is prepared by mixing the following ingredients:

| | |
|---|---|
| Magnesium lanolate | 0.9% |
| Lanolin alcohol | 8.1% |
| Paraffin oil | 38.7% |
| Avocado oil | 0.3% |
| Ozocerite | 2.0% |
| Methyl p-hydroxybenzoate | 0.3% |
| Butyl hydroxy anisole | 0.001% |
| Hydrolysate of Example 1 | 2.0% |
| Sterile demineralised water | balance to 100% |
| Perfume | as desired |

For this purpose the magnesium lanolate is dissolved in the paraffin oil at around 100° C., followed by cooling to 80° C. before the lanolin alcohol and the ozocerite added. The solution is then cooled to 40° C., the avocado oil and the butyl hydroxyl anisole mixed in, and then the hydrolysate of Example 1 dissolved in water and the preservative are added with stirring. The mix is then cooled to ambient temperature with slow stirring and preparation of the emulsion is terminated by addition of the perfume.

This white cream has an anti-dehydrating effect on the skin.

EXAMPLE 5

A revitalising lotion is prepared from the following ingredients:

| | |
|---|---|
| Rose water | 15.00% |
| Glycerin | 5.00% |
| Methyl p-hydroxybenzoate | 0.15% |
| Hydrolysate of Example 1 | 2.00% |
| Perfume + solubiliser | as desired |
| Sterile demineralised water | balance to 100% |

The methyl p-hydroxybenzoate is first dissolved in the sterile demineralised water at 90° C. and, after cooling to 35° C., the glycerin, the rose water and the hydrolysate of Example 1 are added with moderate stirring until a homogeneous dispersion is obtained. Perfume is added last.

EXAMPLE 6

A cleansing milk is prepared by mixing the following ingredients:

| | | |
|---|---|---|
| 1. | Purcellin oil (Dragoco) | 3.0% |
| | Paraffin oil | 7% |
| | Isopropyl palmitate | 5% |
| | Glycerol stearate | 2% |
| | Stearic acid | 1.4% |
| | Triethanolamine | 0.7% |
| 2. | Carbopol 941 ® | 0.7% |
| | Triethanolamine | 0.7% |
| | Methyl p-hydroxybenzoate | 0.2% |
| | Sterile demineralised water | balance to 100% |
| 3. | Hydrolysate of Example 1 | 2.0% |
| | Sterile demineralised water | 30.0% |
| 4. | Perfume | as desired |

This cleansing milk is prepared by dissolving the fat phase (1) kept at 90° C. with vigorous stirring in the homogeneous and neutralised Carbopol gel (2) which itself is kept at 80° C. After the emulsion has formed, it is cooled to 40° C. to introduce with stirring the solution of the hydrolysate of Example 1 (3) and the perfume (4).

The cleansing milk thus obtained has a softening effect.

EXAMPLE 7

A beauty mask is prepared by mixing the following ingredients:

| | | |
|---|---|---|
| 1. | Kaolin | 20.0% |
| | Bentonite | 3.0% |
| | Cetyl alcohol | 2.0% |
| | Sodium lauryl sulphate | 0.2% |
| | Glycerin | 8.0% |
| | Methyl p-hydroxybenzoate | 0.2% |
| | Sterile demineralised water | balance to 100% |
| 2. | Hydrolysate of Example 1 | 10.0% |
| | Sterile demineralised water | 20.0% |
| 3. | Perfume | as desired |

The methyl p-hydroxybenzoate is first dissolved in the glycerin and the water of phase (1) at 90° C. The bentonite, the cetyl alcohol, the sodium lauryl sulphate and the kaolin are then dispersed in the resulting solution with vigorous stirring. The whole is then cooled to 40° C. with moderate stirring, after which the aqueous solution of the hydrolysate of Example 1 (2) is introduced. Finally, the perfume (3) is added.

A beauty mask having soothing properties is obtained.

EXAMPLE 8

A sunburn emulsion is prepared by mixing the following ingredients:

| | |
|---|---|
| Paraffin oil | 9.50% |
| Oleic alcohol | 1.00% |
| Glycerol monostearate | 1.00% |
| Stearic acid | 1.00% |
| Carbopol 941 | 0.15% |
| Triethanolamine | 0.65% |
| Propylene glycol | 2.00% |
| p-hydroxy benzoic esters | 0.30% |
| Hydrolysate of Example 1 | 5.00% |
| Water | balance to 100% |

EXAMPLE 9

A sun cream is prepared by mixing the following ingredients:

| | |
|---|---|
| Paraffin oil | 3.00% |
| White petroleum jelly | 4.00% |
| Stearic acid | 3.00% |
| Glycerol monostearate | 2.00% |
| Triglycerides of saturated $C_8$-$C_{12}$ fatty acids (Miglyol 812) | 15.00% |
| Benzylidene camphor | 2.50% |
| p-hydroxy benzoic esters | 0.30% |
| Propylene glycol | 2.00% |
| Triethanolamine | 0.70% |
| Hydrolysate of Example 1 | 3.00% |
| Water | balance to 100% |

EXAMPLE 10

An after-shave balm is prepared by mixing the following ingredients:

| | |
|---|---|
| Carbopol 940 | 0.4% |
| Hydrolysate of Example 1 | 2.0% |
| Isopropyl myristate | 2.0% |
| 96% alcohol | 20.0% |
| Methyl p-hydroxybenzoate | 0.1% |
| Triethanolamine | 0.4% |
| Water | balance to 100% |

EXAMPLE 11

A baby lotion is prepared by mixing the following ingredients:

| | |
|---|---|
| Glycerol monostearate | 4.00% |
| N—(stearoyl-colaminoformyl-methyl)-pyridinium chloride (Emcol E 607 S) | 1.00% |
| Paraffin oil | 5.00% |
| Lanolin | 1.00% |
| Propoxylated cetyl alcohol (Procetyl AWS) | 0.5% |
| Glycerol | 5.00% |
| Hydrolysate of Example 1 | 1.00% |
| Water | balance to 100% |

EXAMPLE 12

A synthetic soap bar is prepared by mixing the following ingredients:

| | |
|---|---|
| Fatty esters of sodium isethionate (Igepon A) | 46.10% |
| Stearic acid | 20.00% |
| Glycerin | 15.00% |
| Titanium dioxide | 0.10% |
| Soya lecithin | 5.00% |
| Hydrolysate of Example 1 | 3.00% |
| Perfume | 0.80% |
| Water | 10.00% |

We claim:

1. In a composition for topical administration containing a carrier and an active ingredient, the improvement which comprises the active ingredient being a hydrolysate of lactalbumin obtained solely by the action of an endopeptidase, said hydrolysate consisting essentially of peptides having a molecular weight of from 200 to 5,000 and being present in the composition in a proportion of from 0.5 to 25% by weight, expressed as dry weight of hydrolysate in the composition.

2. A composition as claimed in claim 1, characterised in that it contains the hydrolysate in a proportion of from 2 to 10% by weight, expressed as dry weight of hydrolysate in the composition.

3. A composition as claimed in claim 1, characterised in that the hydrolysate is obtained by hydrolysis of lactalbumin with enzymatically pure trypsin or chymotrypsin.

* * * * *